(12) United States Patent
Peluso

(10) Patent No.: US 7,723,300 B2
(45) Date of Patent: May 25, 2010

(54) REGULATORS OF THE NON-GENOMIC ACTION OF PROGESTERONE AND METHODS OF USE

(75) Inventor: John J. Peluso, Avon, CT (US)

(73) Assignee: University of Connecticut, Farmington, CT (US)

( * ) Notice: Subject to any disclaimer, the term of this patent is extended or adjusted under 35 U.S.C. 154(b) by 267 days.

(21) Appl. No.: 11/732,780

(22) Filed: Apr. 4, 2007

(65) Prior Publication Data

US 2007/0238645 A1 Oct. 11, 2007

Related U.S. Application Data

(60) Provisional application No. 60/789,301, filed on Apr. 5, 2006.

(51) Int. Cl.
*A61K 38/00* (2006.01)
*A61K 38/04* (2006.01)
*C07K 14/00* (2006.01)

(52) U.S. Cl. .................. 514/12; 514/2; 514/13; 514/14; 530/300; 530/324; 530/325; 530/326

(58) Field of Classification Search .................. None
See application file for complete search history.

(56) References Cited

U.S. PATENT DOCUMENTS

| 5,976,837 | A | * | 11/1999 | Jacobs et al. | ................ | 435/69.1 |
| 2005/0033018 | A1 | * | 2/2005 | Lal et al. | ..................... | 530/350 |
| 2005/0074842 | A1 | * | 4/2005 | Kato et al. | ................. | 435/69.1 |

OTHER PUBLICATIONS

RUdinger J, "Characteristics of the amino acids as components of a peptide hormone sequence," Peptide Hormones, JA Parsons Edition, University Park Press, Jun. 1976, pp. 1-7.*
"Designing Your Custom Peptides" from SIGMA GENOSYS, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen Jerman J.C., "A Glimpse of the Holy Grail?", Science, Oct. 23, 1998, 282: 642-643.*
Voet Donald and Voet Judith G., Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and tertiary Structure Prediction, K. Merc, Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," Journal of Molecular Biology, 2002, 324: 373-386.*
Skolnick J and Fetrwo JS, "From genes to protein structure and function: novel applications of computational approached in the genomic era," Trends in Biotechnology, 2000, 18(1): 34-39.*

Chaffkin, L.M. et al.; "Progesterone as an Autocrine/Paracrine Regulator of Human Granulosa Cell Proliferation"; *Journal of Clinical Endrocrinology and Metabolism*; vol. 75, No. 6, 1992, pp. 1404-1408, 1992.
Chaffkin, L.M. et al.; "The Role of Progesterone in Regulating Human Granulosa Cell Proliferation and Differentiation in Vitro"; *Journal of Clinical Endocrinology and Metabolism*; vol. 76, No. 3, 1993, pp. 696-700, 1993.
Peluso, J.J. et al.; "Involvement of an Unnamed Protein, RDA288, in the Mechanism through which Progesterone Mediates, Its Antiapoptotoc Action in Spontaneously Immortalized Granulosa Cells"; *Endocrinology*, 145(6):3014-3022, 2004.
Peluso, John J. et al.; "Expression and Functionof PAIRBP1 Within Gonadotropin-Primed Immature Rat Ovaries: PAIRBP1 Regulation of Granulosa and Luteal Cell Viability"; *Biology of Reproduction*; 73, 261-270 (2005).
Peluso, John J.; "Multiplicity of Progesterone's Actions and Receptors in the Mammalian Ovary"; *Biology of Reproducrtion*; 75, 2-8 (2006).
Peluso, John J. et al.; "Progesterone Membrane Receptor Component 1 Expression in the Immature Rat Ovary and Its Role in Mediating Progesterone's Antiapoptotic Action"; *Endocrinology*, 417(6):3133-3140, 2006.
Barnes, Mack N. et al., "A Pilot Study of Ovarian Cancer Chemoprevention Using Medroxyprogesterone Acetate in an Avian Model of Spontaneous Ovarian Carcinogenesis", Gynecologic Oncology 2002, 87, 57-63.
Cameron, Mark R. et al., "The Steroidogenic and Morphological Effects of Paclitaxel on Cultured Ovarian Cancer Cells", Oncology Research 1995, vol. 7, Nos. 3/4, pp. 145-156.
Chen, Xiaojun et al., "Effect of progesterone combined with chemotherapy of epithelial ovarian cancer", Chinese Medical Journal 2003, 116: 388-91.
Crudden, Gerard et al., "Hpr6 (Heme-1 Domain Protein) Regulates the Susceptibility of Cancer Cells to Chemotherapeutic Drugs", The Journal of Pharmacology and Experimental Therapeutics 2006, vol. 316, No. 1, 448-455.
Crudden, Gerard et al., "Overexpression of the Cytochrome P450 Activator Hpr6 (Heme-1 Domain Protein/Human Progesterone Receptor) in Tumors", Tumor Biol 2005, 26:142-146.
Davis, Michael et al., "Refine of Two Chromosome 11q Regions of Loss of Heterozygosity in Ovarian Cancer", Cancer Research Feb. 15, 1996, 56, 741-744.
Engmann, Lawrence et al., "Progesterone Regulation of Human Granulosa/Luteal Cell Viability by an RU486-Independent Mechanism", The Journal of Clinical Endocrinology & Metabolism 2006, 91(12:4962-4968.
Gabra, H. et al., "Chromosome 11 allele imbalance and clinicopathological correlates in ovarian tumours", British Journal of Cancer 1995, 72:367-375.

(Continued)

*Primary Examiner*—Cecilia Tsang
*Assistant Examiner*—Julie Ha
(74) *Attorney, Agent, or Firm*—Kilpatrick Stockton LLP

(57) ABSTRACT

A progesterone regulator capable of modulating the non-genomic action of progesterone and methods of using the progesterone regulator are described. The progesterone regulator is useful for attenuating progesterone's inhibition of apoptosis and for the treatment of patients having a progesterone-responsive tissue disease such as endometriosis or cancer, particularly ovarian cancer.

9 Claims, 7 Drawing Sheets

OTHER PUBLICATIONS

Gabra, Hani et al., "Loss of Heterozygosity at 11q22 Correlates with Low Progestereone Receptor Content in Epithelial Ovarian Cancer", Clinical Cancer Research Sep. 1995, vol. 1, 945-953.

Hempling, R. E. et al., "Progesterone Receptor Status Is a Significant Prognostic Variable of Progression-Free Survival in Advanced Epithelial Ovarian Cancer", J. Clin. Oncol 1998, 21(5): 447-451.

Ho, Shuk-Mei "Estrogen, Progesterone and Epithelial Ovarian Cancer", Reproductive Biology and Endocrinology 2003, 1:73.

Juengel, J. L. et al., "Molecular regulation of luteal progesterone synthesis in domestic ruminants", Journal of Reproduction and Fertility Supplement 1999, 54: 193-205.

Kim, Ki-Yon et al., "Type ll Gonadotropin-Releasing Hormone Stimulates p38 Mitogen-Activated Protein Kinase and Apoptosis in Ovarian Cancer Cells", The Journal of Clinical Endocrinology & Metabolism 2004, 89:(6):3020-3026.

Lindgren, Peter et al., "Steroid receptors and hormones in relation to cell proliferation and apoptosis in poorly differentiated epithelial ovarian tumors", International Journal of Oncology 2001, 19: 31-38.

Losel, R et al., "Classic and Non-classic Progesterone Receptors are both Expressed in Human Spermatozoa", Cancer Epidemiol Biomarkers Prev 2005, 14(1).

Lukanova, Annekatrin et al., "Endogenous Hormones and Ovarian Cancer: Epidemiology and Current Hypotheses", Cancer Epidemiol Biomarkers Prev 2005, 14(1).

McDonnel, Anna C. et al., "Effects of progesterone on ovarian tumorigenesis in xenografted mice", Cancer Letters 2005, 221:49-53.

Munstedt, Karsten et al., "Steroid Hormone Receptors and Long Term Survival in Invasive Ovarian Cancer", Cancer Oct. 15, 2000, vol. 89, No. 8, 1783-1791.

Peluso, John J. et al., "Progesterone Receptor Membrane Component-1 (PGRMC1) is the Mediator of Progesterone's Antiapoptotic Action in Spontaneously Immortalized Granulosa Cells as Revealed by PGRMC1 Small Interfering Ribonucleic Acid Treatment and Functional Analysis of PGRMC1 Mu", Endocrinology Feb. 2008, 149(2):534-543.

Peluso, John J. et al., "Regulation of Ovarian Cancer Cell Viability and Sensitivity to Cisplatin by Progesterone Receptor Membrane Component-1", J Clin Endocrinol Metab May 2008, 93(5):1592-1599.

Rae, Michael T. et al., "Steroid signalling in the ovarian surface epithelium", Trends in Endocrinology and Metabolism Sep. 2005, vol. 16, No. 7, 327-333.

Rodriguez, Gustavo C. et al., "Effect of Progestin on the Ovarian Epithelium of Macaques: Cancer Prevention Through Apoptosis?", J. Soc. Gynecol. Investig. 1998, 5:271-276.

Salzberg, Marc et al., "Current Concepts of Treatment Strategies in Advanced or Recurrent Ovarian Cancer", Oncology 2005, I8:293-298.

Slotman, Berend J. et al., "Survival of Patients with Ovarian Cancer Apart from Stage and Grade, Tumor Progesterone Receptor Content is a Prognostic Indicator", Cancer 1990, 66:740-744.

Yu, Sunhee et al., "Apoptosis Induced by Progesterone in Human Ovarian Cancer Cell Line SNU-840", Journal of Cellular Biochemistry 2001, 82:445-451.

* cited by examiner

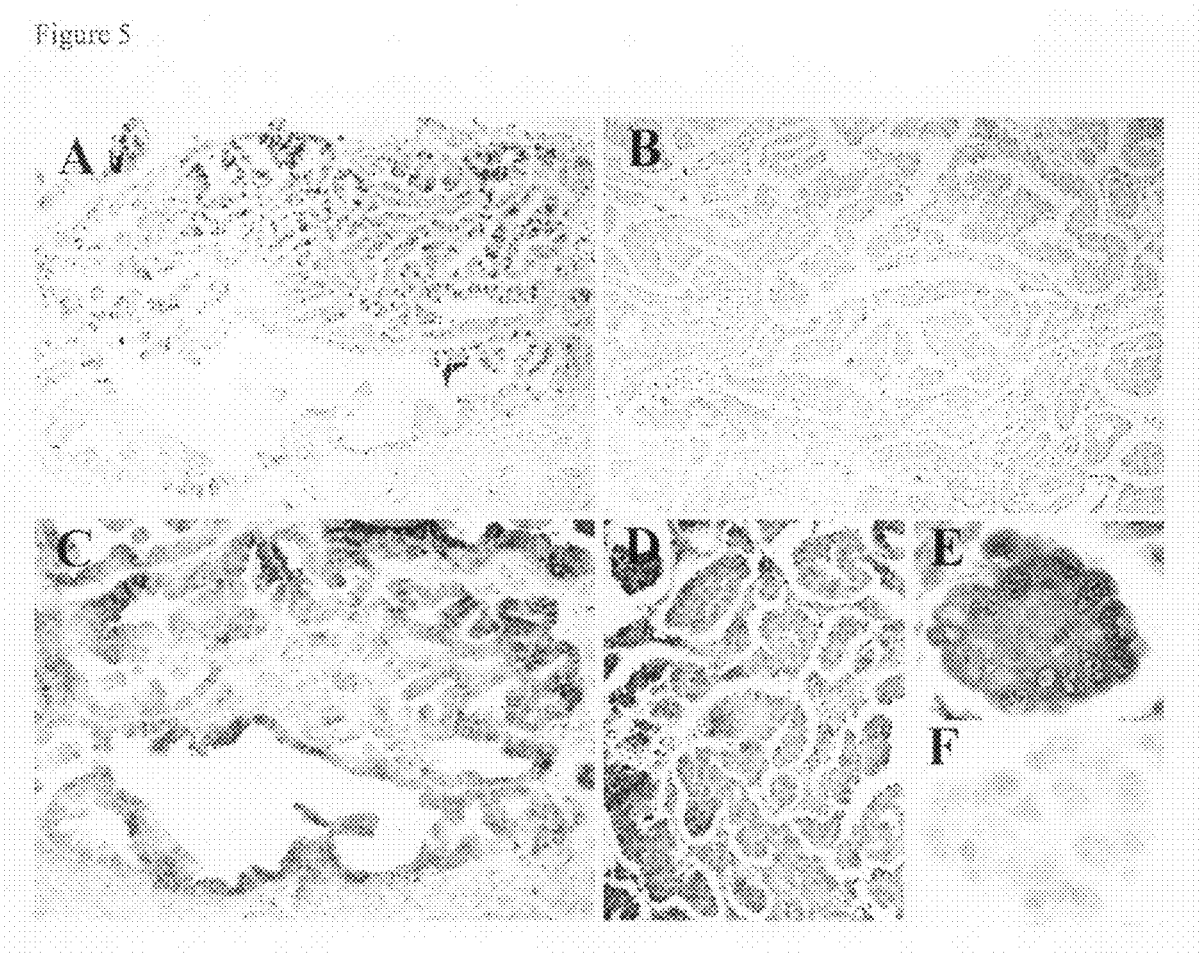

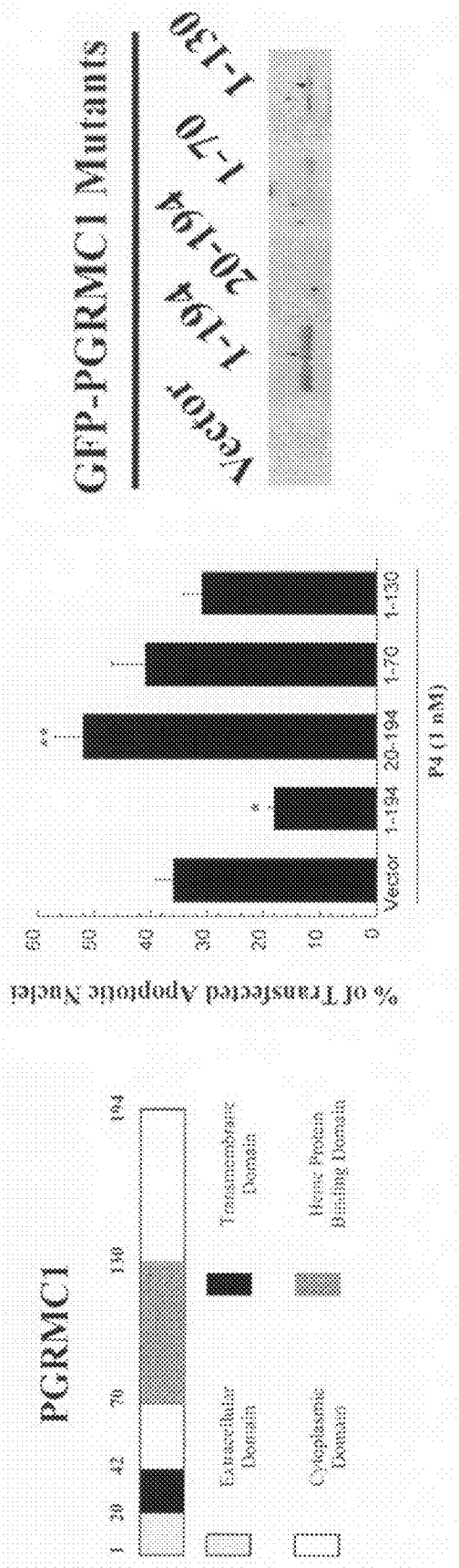

REGULATORS OF THE NON-GENOMIC ACTION OF PROGESTERONE AND METHODS OF USE

CLAIM OF PRIORITY AND CROSS-REFERENCE TO RELATED APPLICATIONS

This application claims priority to U.S. Provisional Patent Application Ser. No. 60/789,301, filed Apr. 5, 2006, which is incorporated herein by reference.

STATEMENT OF GOVERNMENT SUPPORT

This invention was made with government funding under Grant# HD 34383 from the National Institutes of Health. The government has certain rights in the invention.

TECHNICAL FIELD

This application relates to regulators of the non-genomic action of progesterone and use of the regulators for treating progesterone related diseases, such as ovarian cancer. The application more specifically relates to pharmaceutical compositions and methods for inducing progesterone regulated apoptosis.

BACKGROUND OF THE INVENTION

Ovarian cancer kills more women than all the other gynecologic cancers combined and is the fourth leading cause of cancer death among women in the United States. In fact, one in 57 women will be ultimately diagnosed with ovarian cancer. When this cancer is detected early, the five-year survival rate is greater than 90%. However, only 24% of the cancers are detected early. As a result most ovarian cancers are detected in more advanced stages in which the cancer cells have spread outside the ovary. Once the ovarian cancer has spread, the five-year survival rate decreases to less than 25%.

Treatment of patients with ovarian cancer consists of surgery to remove the ovary, the uterus and the tumor. This is usually followed by platinum-based (carboplatin and cisplatin,) chemotherapy. In spite of these intense surgical and chemotherapeutic treatments, the ovarian cancer more often than not recurs. At this point the patients are given salvage chemotherapy and possibly de-bulking surgery to remove the tumors that are usually distributed throughout the peritoneum. Again platinum-based chemotherapy is often used to treat the recurrent ovarian cancers but many of the ovarian cancer cells are resistant to these platinum-based agents, and thus these drugs are relatively ineffective. Increasing the dosage of platinum-based drugs is not an effective approach because these drugs are very toxic.

The overall effectiveness of any regimen for advanced ovarian cancer containing a non-platinum based drug has not yet been established. The inability of the initial chemotherapy to effectively destroy the ovarian cancer results in its recurrence and ultimately the loss of life.

Progesterone (also known as 4-Pregnene-3,20-dione or P4) is a steroid hormone secreted by the ovary. Progesterone influences the function of numerous mammalian organ systems including regulation of the function of the hypothalamus, pituitary, ovary, uterus and mammary gland. Progesterone also affects the various pathological states of these tissues including endometriosis and cancers of the ovary and breast. Depending on the ovarian cell type, progesterone can be either apoptotic (inducing cell death and thereby inhibiting cell growth) or anti-apoptotic (promoting cell growth). It has been observed that progesterone protects against ovarian cancer.

Progesterone regulates the function of the normal and neoplastic mammalian ovary through genomic (or nuclear) and non-genomic (or membrane-initiated) mechanisms. In the genomic mechanism, progesterone binds and activates progesterone receptors (PGR), namely progesterone receptors A and B (PGR-A and PGR-B), which translocate to the nucleus of the cell where they function as transcription factors, inducing the expression of numerous specific genes. In the non-genomic mechanism, progesterone also evokes rapid responses by binding to membrane receptors, including Progesterone Receptor Membrane Component-1 (PGRMC1), which was initially identified as a membrane progesterone binding protein in liver. PGRMC1 forms a progesterone receptor complex with Plasminogen Activator Inhibitor mRNA Binding Protein-1 (PAIRBP1).

The genomic mechanism of progesterone is independent from its non-genomic mechanism. It is generally believed that the protective action of progesterone against ovarian cancer is achieved through PGR in the genomic mechanism. However, it has also been recognized that PGR is expressed within the ovary in a cell specific and hormonally regulated manner. One of the major pharmaceutical agents developed on the basis of PGR's genomic actions is RU486. However, the effectiveness of this pharmaceutical agent in the treatment of ovarian cancer is questionable.

Therefore, there is a great need for pharmaceutical compositions and methods to improve the effectiveness of chemotherapy to treat ovarian cancer by regulating the action of progesterone.

SUMMARY OF THE INVENTION

Compositions containing regulators of the non-genomic actions of progesterone, and methods of use are provided herein. In particular, the progesterone regulators act through a previously unrecognized progesterone receptor complex that is located on the plasma membrane. Also provided are compositions and methods of using regulators to inhibit progesterone non-genomic actions, such as for the treatment of diseases involving progesterone-responsive tissues. The progesterone regulators are useful for improving the effectiveness of chemotherapy for the treatment of progesterone-related cancers, particularly for cancers of the ovary, uterus or breast. The progesterone regulators are also useful as agents for the diagnosis and prognosis of progesterone-responsive diseases. When used for pharmaceutical administration, the compositions described herein contain the progesterone regulator in a pharmaceutically acceptable carrier.

The progesterone regulator achieves the desired inhibition of progesterone non-genomic action by impeding the binding of progesterone to a progesterone receptor complex on a progesterone-responsive diseased tissue such as a tumor or diseased endometrial tissue. Progesterone binding is impeded by blocking the binding of progesterone to the progesterone receptor complex, by reducing the amount of one or more proteins that make up the receptor complex or by inhibiting the interactions of molecules to form the receptor complex. In one embodiment, the progesterone regulator binds to the progesterone receptor complex to block the binding of progesterone to the receptor. In another embodiment, the progesterone regulator reduces the production of PGRMC1, PAIRBP1, or both. In yet another embodiment, the progesterone regulator interferes with the interaction between PGRMC1 and PAIRBP1 to inhibit formation of the receptor complex. The inhibitory effect may be accomplished by depleting or blocking the extracellular domain of PGRMC 1.

Suitable progesterone regulators include, but are not limited to, peptides and nucleic acid molecules. Preferably, the progesterone regulator is a chemical compound, a peptide, a DNA molecule encoding a peptide, a nucleic acid molecule such as a small interfering RNA (siRNA), a protein, or an antibody. Suitable progesterone regulators may be based on the discovery of critical sequences in PGRMC1 required for interaction with PAIRBP1 and/or required for interaction with progesterone. For example, the first 20 amino acids of PGRMC1 make up the extracellular domain of this protein and have the amino acid sequence of SEQ ID NO:1 or SEQ ID NO:2. Useful progesterone regulators include peptides or DNA molecules encoding peptides having an amino acid sequence with at least about 60%, 80% or 90% homology to the extracellular domain of PGRMC1. Suitable progesterone regulators also include antibodies that bind to the extracellular domain of PGRMC1.

In one embodiment, the progesterone regulator is a peptide and the composition may optionally contain an additional peptide that directs the progesterone regulator to the cancer, such as luteinizing hormone. This additional peptide may be coupled to the progesterone regulator, using methods well known to those skilled in the art, such as in a fusion protein.

In addition, the progesterone regulator may optionally be provided in combination with a pharmaceutical agent, such as an anti-cancer drug, to facilitate the agents' specificity for diseased cells that express the progesterone receptor complex.

Treatment of a disease involving progesterone-responsive tissue is achieved by administering one or more of the progesterone regulator compositions described herein. Diseases involving a progesterone-responsive tissue to be treated include endometriosis and cancers, such as but not limited to, cancers of the ovary, uterus or breast.

Also provided herein are methods for the detection of abnormal functionality involved in progesterone's non-genomic actions, which are useful for diagnosing patients having pathological conditions that are likely to respond to chemotherapy and for providing prognostic information.

Accordingly, it is an object of the present invention to provide a progesterone regulator of the non-genomic actions of progesterone.

It is another object of the present invention to provide a progesterone regulator that selectively inhibits the interaction between PGRMC1 and PAIRBP1 on the plasma membrane without influencing nuclear progesterone receptors.

It is another object of the present invention to provide a progesterone regulator that inhibits progesterone's anti-apoptotic effect by targeting PGRMC1.

It is another object of the present invention to identify the specific sites or domains of PGRMC1 that interact with PAIRBP1.

It is yet another object of the present invention to provide a pharmaceutically acceptable composition containing a progesterone regulator.

It is yet another object of the present invention to provide a method of treating diseases involving a progesterone-responsive tissue by administering a pharmaceutically acceptable composition containing a progesterone regulator.

It is yet another object of the present invention to provide a method of treating cancer in which the effectiveness of an anti-cancer chemotherapy is improved by administering a pharmaceutically acceptable composition containing a progesterone regulator and an anti-cancer drug.

These and other objects, features and advantages of the present invention will become apparent after a review of the following detailed description of the disclosed embodiments and the appended claims.

BRIEF DESCRIPTION OF THE FIGURES

FIGS. 5 is a collection of micrographs showing expression of PGR (panels A and B) and PGRMC1 (panels C, D and E) in Stage IIIb (panel A and panel C) and Stage IIIc (panel B, panel D and panel E) ovarian cancers. Each protein is revealed by a brown stain. Panel F is a negative control.

FIG. 7A is a schematic representation of the structural organization of progesterone receptor membrane component-1 (PGRMC1). The numbers above each structure refer to the amino acid number. A series of deletion mutants were constructed and named according to the amino acids that they encode (i.e., 1-194 encodes the entire PGRMC1 molecule). FIG. 7B is a bar graph showing percent transfected cells with apoptotic nuclei. These mutants were transfected into SIGC cells, and SIGC cells that expressed each of these mutants were monitored by their ability to undergo apoptosis. FIG. 7C is a reproduction of a western blot showing the ability of each of these constructs to bind to PAIRBP1. In this assay, each mutant was isolated using GFP affinity beads, and the ability of the mutant to bind PAIRBP1 was assessed.

DETAILED DESCRIPTION OF INVENTION

Figure 1:
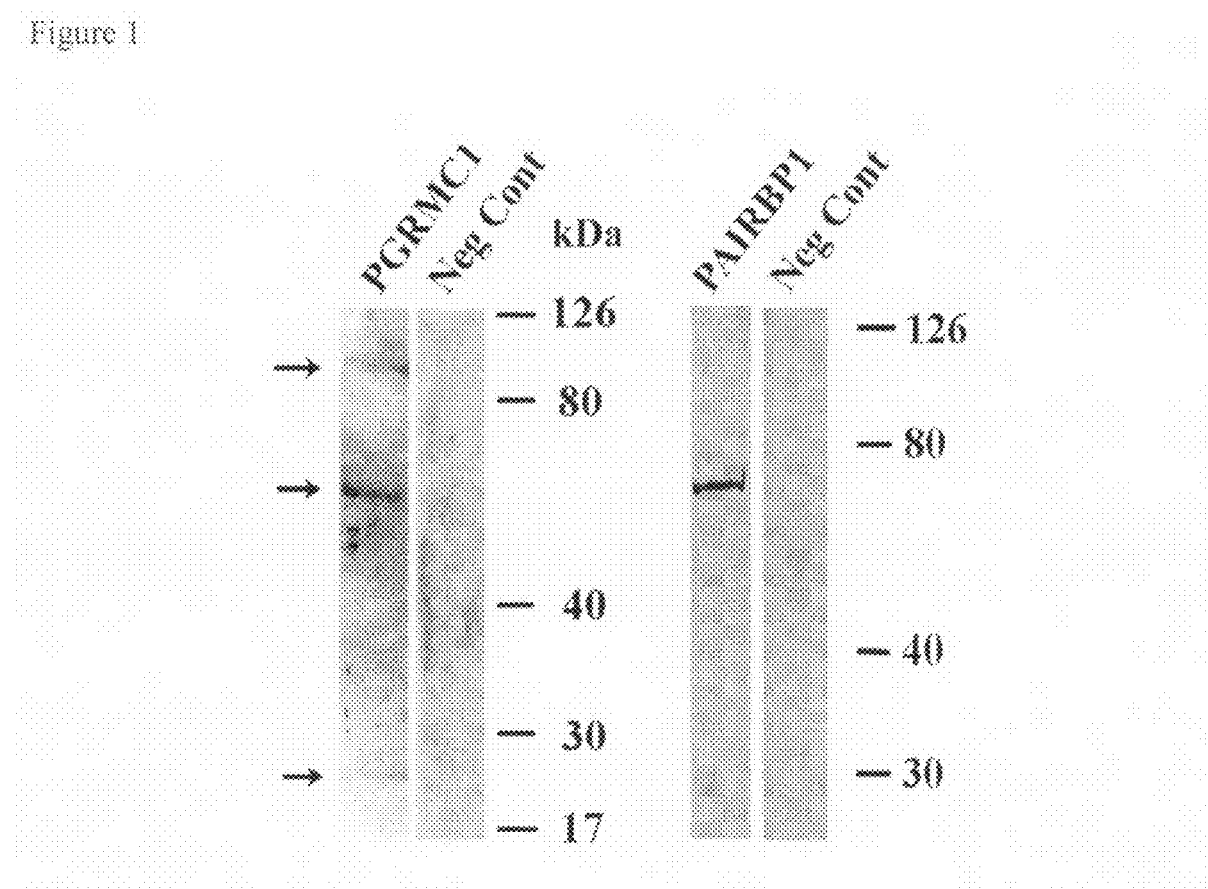
FIG. 1 is a scan of a western blot showing expression of Progesterone Receptor Membrane Component-1 (PGRMC1; left panel) and its binding partner, Plasminogen Activator Inhibitor mRNA Binding Protein-1 (PAIRBP1; right panel), in human granulosa/luteal cells. Note that although PGRMC1 is approximately 28 kDa, it often is detected as a 56 kDa dimer or as an oligomer. These different molecular weight forms of PGRMC1 are indicated by an arrow on the left panel.

Progesterone regulators, or agents, having the ability to modulate or inhibit progesterone non-genomic action are provided. The progesterone regulators described herein inhibit the anti-apoptotic effects of progesterone and are useful for the treatment of diseases involving progesterone-responsive tissues. The progesterone regulators are also useful for improving the effectiveness of chemotherapy used to treat progesterone-related cancers, particularly for cancers of the ovary, uterus or breast. In addition, the progesterone regulators are useful as agents for the diagnosis and prognosis of progesterone-responsive diseases. The attenuation of progesterone's anti-apoptotic action may be achieved by either impairing the binding of progesterone to its membrane receptor or by disrupting the interaction between PGRMC1 and PAIRBP1 on progesterone-responsive disease tissues. This attenuates the anti-apoptotic effects of progesterone and provides a unique method for treating progesterone-supported cell growth and reducing the resistance of cancer cells, including breast and ovarian cancer cells, to chemotherapy.

Compositions

Compositions are provided that contain the progesterone regulator described herein in a pharmaceutically acceptable carrier. As explained above, the progesterone regulator modulates or inhibits progesterone non-genomic action. The progesterone regulator achieves this effect by impeding the function of a progesterone receptor complex on a progesterone-responsive diseased tissue such as a tumor or diseased endometrial tissue. This is achieved by either blocking the binding of progesterone to the receptor complex or by reducing the amount of one or more proteins that form the receptor complex. In one embodiment, the progesterone regulator binds to the progesterone receptor complex in such a way that it directly blocks or impedes the binding of progesterone to the receptor. In another embodiment, the progesterone regulator reduces the production of either PGRMC1, PAIRBP1, or both, thereby inhibiting the formation of the progesterone receptor complex. In yet another embodiment, the progesterone regulator interferes with the interaction between PGRMC1 and PAIRBP1, thereby inhibiting the ability of these molecules to form a functional progesterone receptor complex.

Chemotherapeutic agents such as cisplatin (also known as cis-diamminedichloroplatinum(II)) kill ovarian cancer cells by inducing death by apoptosis. However, cisplatin fails to kill 100% of the cancer cells and, inadvertently, induces apoptosis in normal cells, causing poor therapeutic results, and adverse side effects. Normally, PGRMC1 interacts with PAIRBP1 to form the progesterone receptor complex. Progesterone binds to this progesterone receptor complex and activates intracellular survival pathways that prevent apoptosis. Because some cells, such as ovarian cancer cells, synthesize progesterone, ovarian cancer cells establish conditions that promote their own survival, making them more resistant to chemotherapeutic agents such as cisplatin. It has been discovered that the progesterone produced by these cancer cells counteracts the apoptotic effects of cisplatin, thereby allowing the cancer cells to thrive.

It will be appreciated that the terms "progesterone regulator" and "progesterone agent" as used herein are interchangeable and are defined herein as any chemical compound or biological molecule capable of selectively regulating the action of progesterone through a non-genomic mechanism without affecting progesterone's genomic mechanism. Suitable biological molecules having the desired non-genomic inhibitory effect include, but are not limited to, peptides and nucleic acid molecules. "Progesterone non-genomic action" is defined herein as non-nuclear action or action through a mechanism other than via PGR. For example, progesterone non-genomic action may occur by way of a membrane receptor or in a progesterone-responsive tissue.

Preferably, the progesterone regulator is a chemical compound, a peptide, a DNA molecule encoding a peptide, a nucleic acid molecule such as a small interfering RNA (siRNA), a protein, or an antibody. In one embodiment, the progesterone regulator impedes or blocks the binding of progesterone to the progesterone receptor complex, preferably by the binding of the progesterone regulator, most likely compose of a peptide or protein, to the progesterone receptor complex. In another embodiment, the progesterone regulator acts by depleting the expression of PGRMC1 or PAIRBP1. The reduced production of either or both of these proteins results in a reduction in the amount of functional progesterone receptor complex available for binding to progesterone. In another embodiment, the progesterone regulator inhibits the interaction or binding between PGRMC1 and PAIRBP1 to form the progesterone receptor complex. In the absence of this complex, progesterone fails to bind to cells of the diseased tissue, and progesterone's ability to block apoptosis is impeded. In this way, the progesterone regulator causes cells of the diseased tissue to become more susceptible to chemotherapies relying on apoptosis, such as platinum-based chemotherapies, particularly cisplatin. Accordingly, blockage of the progesterone binding site on the progesterone receptor complex, reduced expression of the molecules that interact to form the progesterone receptor complex, and disruption of the interaction between PGRMC1 and PAIRBP1 may lead to the complete attenuation of progesterone's ability to inhibit apoptosis.

Suitable progesterone regulators may be based on the discovery of critical sequences in PGRMC1 required for interaction with PAIRBP1 and/or required for interaction with progesterone. A series of GFP-PGRMC1 mutants were generated to identify the amino acid sequence within PGRMC1 that interacts with PAIRBP1 (FIGS. 7B and 7C). The numbers associated with each mutant denote the amino acids they encode. While the wild-type (1-194) transduces progesterone's action, the deletion of any section results in an inability to mediate progesterone's action. This suggests that there are different functional domains throughout PGRMC1. The first 20 amino acids of PGRMC1 make up the extracellular domain of this protein. Depletion of the first 20 amino acids of PGRMC1, leads to a rate of apoptosis that is even greater than the vector alone or other mutants. Furthermore, the extracellular domain (FIG. 7A) of PGRMC1, is required for its interaction with PAIRBP1. Based on a BLAST search, the sequence of the first 20 amino acids of PGRMC1 is unique and appears to occur only in the PGRMC1 protein.

The first 20 amino acids of PGRMC1 have the amino acid sequence MAAEDVVATGADPSELELLL (SEQ ID NO:1). In an alternative embodiment, the first 20amino acids of PGRMC1 have the amino acid sequence MAAEDVVATGADPSDLESGG (SEQ ID NO:2).

Useful progesterone regulators inhibit or prevent the binding between PGRMC1 and PAIRBP1 or the expression of one or more of these molecules. Suitable progesterone regulators include PGRMC1 specific siRNA molecules capable of depleting PGRMC1 in progesterone-supported cancer cells. Useful progesterone regulators also include agents, such as chemical compounds or biological molecules, that are capable of blocking progesterone from binding specifically to cancer cells, such as antibodies against either PGRMC1 or PAIRBP1. Other regulators include peptides or DNA molecules encoding peptides having an amino acid sequence with at least about 60%, 70%, 80% or 90% homology with the extracellular domain (i.e. the first 20 amino acids) of PGRMC1. These peptides are useful as progesterone regulators because they may compete with PGRMC1 for the ability to interact with PAIRBP1. Preferably, the progesterone regulator is a peptide or DNA encoding a peptide having an amino acid sequence with at least about 60%, 70%, 80% or 90% homology to the first 20 amino acids of PGRMC1, set forth above as SEQ ID NO:1 or, alternatively, SEQ ID NO:2.

Alternatively, the progesterone regulator is an antibody that binds to the extracellular domain of PGRMC1 to block or impair the ability of PGRMC1 to interact with PAIRBP1 to form the progesterone receptor complex. Preferably, the progesterone regulator is an antibody that binds to the first 20 amino acids of PGRMC1. More preferably, the progesterone regulator is an antibody that binds to the domain of PGRMC1 having the amino acid sequence of SEQ ID NO:1 or 2.

Although not wishing to be bound by the following, it is believed that disruption of the receptor complex of PGRMC1 and PAIRBP1 in ovarian cancer cells decreases the progesterone-supported viability of the cancer cells. PGRMC1 and its binding partner, PAIRBP1, are potential targets that could block progesterone's anti-apoptotic action, thereby reducing the viability of cancer cells and improving the effectiveness of chemotherapy.

When the progesterone regulator is a peptide, the composition may optionally contain an additional peptide sequence that includes all or part of a sequence encoding a peptide that directs the progesterone regulator to the diseased tissue or cancer, particularly a progesterone-related cancer. For example, the receptor for the luteinizing hormone (LH) is highly expressed in ovarian and breast cancers. Therefore, a fusion protein composed of the progesterone regulator coupled to LH is useful for more selectively delivering the progesterone agent to the ovarian or breast cancer cells.

In addition, the progesterone regulator (such as a peptide or siRNA) may optionally be provided in combination with and/or covalently linked to a chemotherapeutic agent, or an anti-cancer drug, to facilitate the agents' specificity for cancer cells that express the progesterone receptor complex. In this way, the progesterone regulator functions as an adjunct treatment. Chemotherapeutic agents useful in combination with the progesterone regulator include those administered for the treatment of progesterone-related cancers such as, but not limited to, platinum-based agents such as carboplatin and cisplatin.

Ideally, the composition is a pharmaceutical composition containing the progesterone regulator described herein in combination with a pharmaceutically acceptable carrier for administration to a mammal, such as a human patient, as described in more detail below.

Methods of Treatment

Treatment of a disease involving a progesterone-responsive tissue is achieved by administering the pharmaceutical composition provided herein, which contains a progesterone regulator capable of attenuating a non-genomic action of progesterone. Suitable compositions and progesterone regulators are described herein.

Diseases involving a progesterone-responsive tissue to be treated include endometriosis and cancers, such as but not limited to, cancers of the ovary, uterus or breast.

An ovarian cancer patient may be treated conventionally with surgery, radiation or chemotherapy, and then a pharmaceutical composition containing a progesterone agent is subsequently administered to the patient to reduce progesterone-supported resistance of the cancer cells.

The progesterone regulators described herein can be provided as substantially purified compositions and placed in pharmaceutically acceptable formulations using formulation methods known to those of ordinary skill in the art. These formulations can be administered by standard routes. In general, the compositions may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the progesterone regulator may be incorporated into biodegradable polymers allowing for sustained release, the polymers being implanted in the vicinity of where drug delivery is desired, for example, at the site of a tumor or implanted for systemic slow release. Osmotic minipumps may also be used to provide controlled delivery of high concentrations of the progesterone regulator, through cannulae to the site of interest, such as directly into a metastatic growth or into the vascular supply to that tumor.

The effective dosage of the progesterone regulator provided herein will depend on the disease state or condition being treated and other clinical factors such as weight and condition of the human or animal and the route of administration of the agent. Depending upon the half-life of the agent in the particular animal or human, it can be administered between several times per day to once a week. It is to be understood that the methods provided herein have applications for both human and veterinary use. The methods described herein contemplate single as well as multiple administrations, given either simultaneously or over an extended period of time.

The progesterone agent formulations provided herein include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The progesterone agent formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions, which may contain anti-oxidants, buffers, bacteriostats and solutes that render the formulation isotonic with the blood of the intended recipient; and aqueous and non-aqueous sterile suspensions, which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the pharmaceutical composition may include other agents conventional in the art having regard to the type of formulation in question.

Methods of Diagnosis

Early diagnosis and treatment of cancer is known to enhance survival. Methods for the detection of abnormal functionality involved in progesterone's non-genomic actions are useful for diagnosing patients having pathological conditions that are likely to respond to chemotherapy and for providing prognostic information. The abnormal functionalities include PGRMC1's lack of an extracellular domain, progesterone's failure to bind specifically to PGRMC1, PGRMC1's failure to interact with PAIRBP1, and PGRMC1's failure to attenuate progesterone's anti-apoptotic activity. Suitable pathological conditions for diagnosis include diseases such as endometriosis and cancers involving progesterone-responsive tissues. The diagnostic methods include but not limited to the following techniques: competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry.

PGRMC1 is expressed in human ovarian cancer cells, including human ovarian cancer cell line Ovcar-3 and ovarian epithelial cell line referred to as spontaneously immortalized granulosa cells (SIGCs), as well as many tumors from patients having Stage I to IV serious ovarian cancers, in which PGR is not expressed. Even in the PGR positive tumors, very few areas within the entire tumor are positive for PGR. In contrast, as shown in the examples below, ovarian cancers express PGRMC1 regardless of whether or not they express PGR (FIG. 5). Moreover, PGRMC1 is detected in virtually 100% of the tumor cells in these tumors. This inverse relationship between PGR and PGRMC1 expression is supported by the observation that the expression of PGRMC1 is greater in PGR knockout mice than their wild-type controls. Interestingly, progesterone prevents the formation of ovarian tumors but does not affect their development once established. This is consistent with the observation that early stage tumors express PGR but that as they develop PGR expression is lost and only PGRMC1 is expressed. Therefore, PGRMC1 plays an important role in ovarian cancer development.

Detection of a disrupted interaction between PGRMC1 and PAIRBP1 or a disrupted progesterone binding to PGRMC1 is useful for identifying and diagnosing cancers that are likely to be responsive to chemotherapy. The detection may be performed using methods known to those skilled in the art such as by the use of a labeled antibody. For example, a monoclonal antibody may be generated against a peptide of SEQ ID NO:1 or SEQ ID NO:2. An ovarian tumor tissue sample may be obtained from a patient and incubated with the antibody. The bound antibody is then detected quantitatively using conventional detection methods for the presence of the extracellular domain of PGRMC1. The absence of the extracellular domain from PGRMC1 disrupts progesterone's non-genomic action such as progesterone-supported resistance of cancer cells to chemotherapy.

In addition, an application of FRET analysis may provide additional information as to whether the PGRMC1 interacts with PAIRBP1. Further, an analysis of potential mutations in PGRMC1 or PAIRBP1 gene in an ovarian tissue sample using conventional methods can also be carried out. Lack of the interaction between PGRMC1 and PAIRBP1 or progesterone specific binding to PGRMC1 in a tumor tissue from a patient provides valuable information as to whether the patient is likely to respond to chemotherapy.

The diagnostic and prognostic methods provided herein also include a detection of PGRMC1's down regulation of progesterone's anti-apoptotic effect (i.e., progesterone's inhibition of programmed cell death). To determine whether PGRMC1 regulates progesterone's biological actions such as its anti-apoptotic effect through the non-genomic mechanism in tumor cells, siRNAs for PGRMC1 and/or PAIRBP1 may be introduced into the ovarian cancer cells to deplete the expression of PGRMC1 and/or PAIRBP1. The effect of changing the expression levels of these proteins on progesterone's ability to inhibit apoptosis may then be monitored. Detection of an increasing percentage of apoptotic tumor cells from a patient upon depletion suggests that the patient is likely to respond to chemotherapy.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

PGRMC1 Mediates Progesterone's Anti-apoptotic Effect

Experiments with human granulosa/luteal cells were conducted by using the methods as described in detail below or, in instances where only brief descriptions are provided below, by using methods that have been published and are well known in the field.

Patients

Granulosa/luteal cells were obtained by follicular aspiration from women with various infertility diagnoses undergoing in vitro fertilization under a protocol approved by the Institutional Review Board of the University of Connecticut Health Center. Briefly, patients were treated with a GnRH (gonadotropin releasing hormone) analog (Lupron) during the luteal phase to suppress ovarian function (i.e. estradiol levels of <75 pg/ml and no follicles >10 mm). Once ovarian function was suppressed then the patients were treated with gonadotropins as outlined by Schmidt et al. Patients that have two to three follicles with an 18 mm average diameter and estradiol values of between 2500 and 5,500 pg/ml were injected with human chorionic gonadotropin (hCG). Thirty-five hours after hCG administration, the follicles were aspirated under transvaginal ultrasound guidance.

Cell Preparation and Culture

After the oocytes were removed, follicular aspirates were pooled and centrifuged at 250×g for 10 minutes. The cell pellet was resuspended in serum-free culture medium, layered on HISTOPAQUE-1077 and centrifuged for 30 minutes at 400×g. After centrifugation, the opaque interface containing the granulosa/luteal cells was carefully aspirated and transferred into a 15 ml sterile conical centrifuge tube. The cells were then washed by resuspending the cells in 12 ml of PBS and centrifuging them at 250×g for 10 minutes. This was repeated two additional times. The cell pellet was then resuspended in 1 ml of 0.25% trypsin-EDTA solution and incubated for 5 minutes to dissociate the cells. After trypsinization, 5 ml of serum-supplemented medium was added and the cells were centrifuged at 250×g for 10 minutes. The cells were then resuspended in serum-supplemented medium, counted in a hemacytometer and resuspended to yield a final concentration 1 million cells/ml.

Plastic lab-tek slides (BD Bioscience, Bedford, Mass.), which had been previously coated with Growth Factor Reduced Matrigel Matrix (BD Bioscience, Bedford, Mass.), were plated at about 60,000 cells per well in 0.5 ml of serum-supplemented medium with 2 U/ml (IU) of hCG. The medium was changed after 24 hours to remove any remaining blood cells or non-attached granulosa/luteal cells and the cultures continued for two additional days. The cultures were then subjected to the various experimental treatments as outlined below.

Detection of Apoptotic Nuclei

Both TUNEL and in situ DNA staining were used to identify apoptotic nuclei. For the TUNEL assay human granulosa/luteal cells were cultured for 5 hours in serum-free medium and then fixed in 10% formalin. The cells were stained using the Apoptag Peroxidase In Situ kit staining according to manufacture's instructions (Chemicon, Temecula, Calif.). In situ DNA staining was done by adding hydroethidine directly to the culture medium at a final concentration of 3.5 µg/ml. The cultures were incubated for 15 minutes at room temperature in the dark. After staining, the cells observed under epi-fluorescent optics. Under these conditions only cells with condensed or fragmented nuclei were stained intensely with hydroethidine. These cells were considered to be apoptotic in accordance with prior publications in the field. At least 100 cells/culture well were counted and the percentage of apoptotic nuclei in each well determined.

Immunocytochemical and Western Blot Analysis

To localize the Progesterone Receptor (PGR), cells were fixed with 10% formalin and permeabilized with 0.1% Triton-X. Endogenous peroxidase activity was blocked by incubating the cells in 0.3% peroxidase in methanol for 30 minutes at room temperature. To reduce non-specific staining, the slides were incubated with powerblock (Biogenex, San Roman, Calif.) and then incubated overnight with a 1:50 dilution of PGR antibody (Ab-8, Lab Vision/Neomarker, Fremont, Calif.). The cells were then incubated with biotinylated goat anti-rabbit IgG followed by incubation for 30 minutes with ABC reagent (Vector Laboratories, Burlingame, Calif.). The slides were developed using a diaminobenzidine-peroxidase substrate for 5 minutes followed by light counter-staining with Methyl Green. The presence of PGR was revealed by the presence of a reddish-brown precipitate.

Expression and localization of PGRMC1 and PAIRBP1 was assessed by Western blot and confocal immunocytochemistry, respectively. For Western blot studies, human granulosa/luteal cells were lysed in RIPA buffer (50 mM TRIS, 150 mM sodium chloride, 1.0 mM EDTA, 1% Nonidet progesterone and 0.25% sodium-deoxycolate; pH 7.0) which was supplemented with complete protease inhibitor cocktail (Roche, Mannheim, Germany) and phosphatase inhibitor cocktail 1 (Sigma Chemical Co., St Louis, Mo.) and then centrifuged at 1,000×g at 4° C. for 5 minutes. The supernatant was collected and centrifuged at 100,000×g at 4° C. for 1 hour. Twenty µg of this membrane preparation was run on a 12% acrylamide gel and transferred to nitrocellulose. The nitrocellulose was then incubated with 5% non-fat dry milk overnight at 4° C. The nitrocellulose blot was then incubated with either the chicken PAIRBP1 antibody at a dilution of 1:2000 or the rabbit PGRMC1-NT antibody (1:2000) (published method) for 1 hour at room temperature. Western blots were processed using a horseradish peroxidase goat anti-chicken IgY (1:50,000; Aves Labs, Tigard, Oreg.) or a horseradish peroxidase goat anti-mouse antibody (1:10,000). KPL LumiGlo detection system was used to reveal the presence of both proteins. As a negative control, an immunodepleted antibody preparation or rabbit IgG was used in place of the PAIRBP1 antibody and PGRMC1-NT antibody, respectively.

For confocal studies human granulosa/luteal cells were grown on glass coverslips within 35 mm culture dishes. After three days of culture these cells were washed and then fixed in 10% formalin and permeabilized as previously described (published method). The coverslips were then incubated overnight at 4° C. with the antibodies to PAIRBP1 (1:50), PGRMC1-NT (1:50) or both. After washing to remove the primary antibodies, the coverslips were incubated for 1 hour at room temperature in the dark with Alexa Fluor 633-goat anti-chicken IgG (1:100) and Alexa Fluor 488-goat anti-rabbit IgG (1:100). The coverslips were again washed and observed under the confocal microscopy. Negative controls were also processed as described above with the exception that the immunodepleted antibody preparation or IgG was used in place of the PAIRBP1 or PGRMC1-NT antibody, respectively.

PGRMC1 and PAIRBP1 Blocking Antibody Study

Human granulosa/luteal cells were plated on lab tek slides and cultured for three days as previously described. The cells were then washed in serum-free medium and cultured for one hour with either serum-free media supplemented with rabbit IgG (20 µg/ml), antibody to PGRMC1 (20 µg/ml), IgY (34 µg/ml) or an antibody to PAIRBP1 (34 µg/ml) in the presence or absence of progesterone (0.1 µM). After culture the cells were raised in Krebs/Hepes buffer and stained to detect apoptotic nuclei as taught by Engmann et al., *J. of Clinical Endocrinology and Metabolism* 91(12): 4962-4968 (2006). One hundred cells in each chamber were counted and the percentage of apoptotic nuclei determined as previously described.

Statistical Analysis

All experiments were repeated at least three times with each experiment yielding essentially identical results. When appropriate, the data were pooled to generate means±standard errors and analyzed by either a Student $^3t^2$ tests when an experiment consisted of two treatment groups or a one-way ANOVA followed by a Student-Newman-Keuls test, if more than two treatments groups were being compared. P values of less than 0.05 were considered to be significant.

Serum withdrawal induced human granulosa/luteal cells to rapidly undergo apoptosis as assessed by both TUNEL assay and in situ DNA staining. About 10% of the human granulosa/luteal cells maintained in serum-supplemented medium for three days were considered to be apoptotic. This percentage increased to about 30% within five hours of serum withdrawal (p<0.05). Time-course studies revealed that a similar increase in apoptosis was observed after one hour in serum-free medium and that this increase was suppressed by progesterone. Moreover, progesterone at all doses tested suppressed apoptosis. The lowest effective dose was 10 nM.

Immunocytochemical analysis revealed that after three days of culture about 20% of the human granulosa/luteal cells expressed the PGR. Moreover, 25 and 50 µM doses of the PGR antagonist, RU486, increased the percentage of apoptotic nuclei to greater than 70%. Progesterone at 1 µM could not override the effect of RU486 at these high concentrations. Interestingly, 5 µM RU486 did not increase the percentage of apoptotic nuclei compared to control and 1 µM progesterone was still capable of suppressing serum-withdrawal induced apoptosis. Finally, when human granulosa/luteal cells were deprived of progesterone for 15 or 30 minutes, progesterone's ability to prevent apoptosis was lost.

Figure 2:
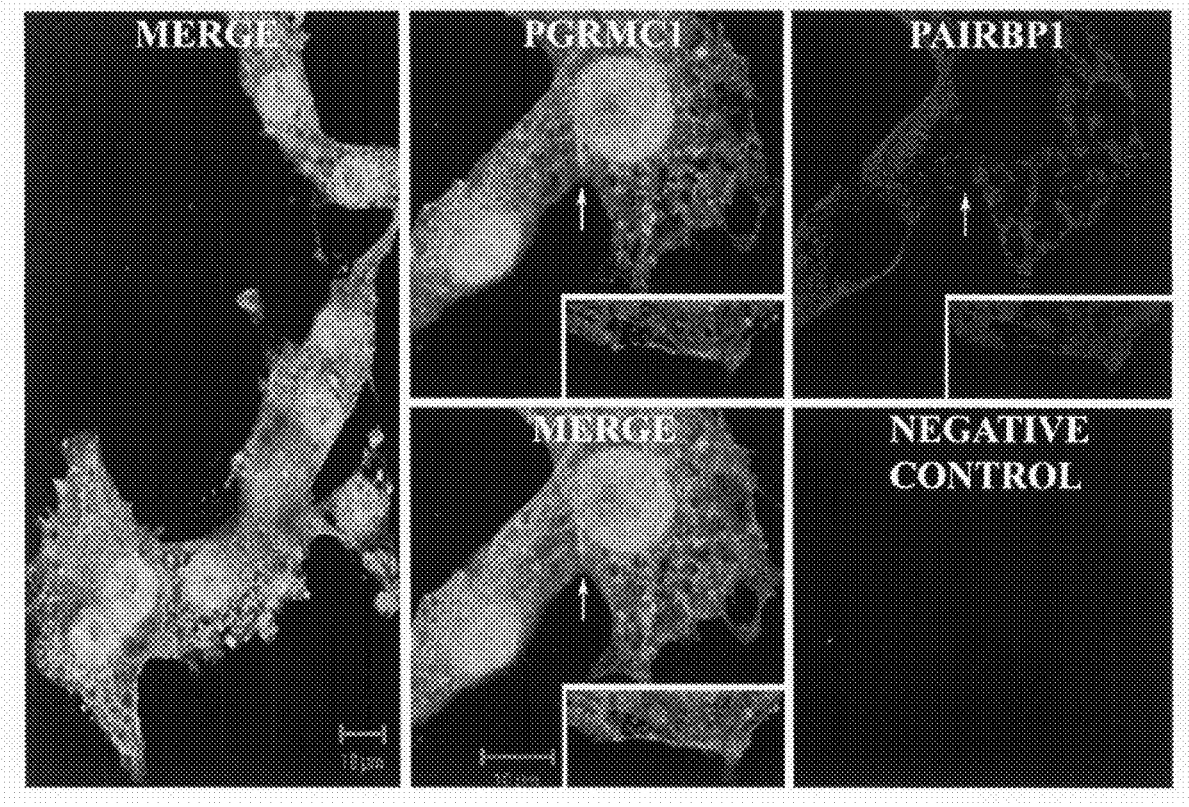
FIG. 2 is a scan of a micrograph showing immunocytochemical localization of PGRMC1 and PAIRBP1 in human granulosa/luteal cells after three days of culture. The presence of PGRMC1 was revealed by a green fluorescence, while PAIRBP1 was detected by a red fluorescence. The yellow-orange fluorescence in the panels labeled MERGE reveals cellular sites where the two proteins co-localize. The panel on the left shows several human granulosa/luteal cells with all cells expressing both PGRMC1 and PAIRBP1. The insert shows a higher magnification of the periphery of a single human granulosa/luteal cell.

Western blot and confocal analysis revealed that both of these proteins were expressed in human granulosa/luteal cells (FIGS. 1 and 2, respectively). Unlike PGR expression, virtually all the human granulosa/luteal cells expressed PGRMC1 and PAIRBP1 (FIG. 2). These proteins co-localized near the plasma membrane as well as to a fibrous network within the cytoplasm (FIG. 2). Although these proteins were often co-localized, PGRMC1 did not appear to associate with PAIRBP1 at the points of cell-cell contact or in the nucleus (FIG. 2). The nuclear localization of PGRMC1 was particularly intense. Note that the exclusive localization of PGRMC1 to the areas of cell-cell contact that is illustrated in the higher magnification merged image (arrow) is not clearly seen in the lower magnification merged image. This is because the cells do not form a flat monolayer and it is impossible to observe all the cells in the precise focal plane that reveals the localization of PGRMC1 to the site of cell-cell contact.

Figure 3:
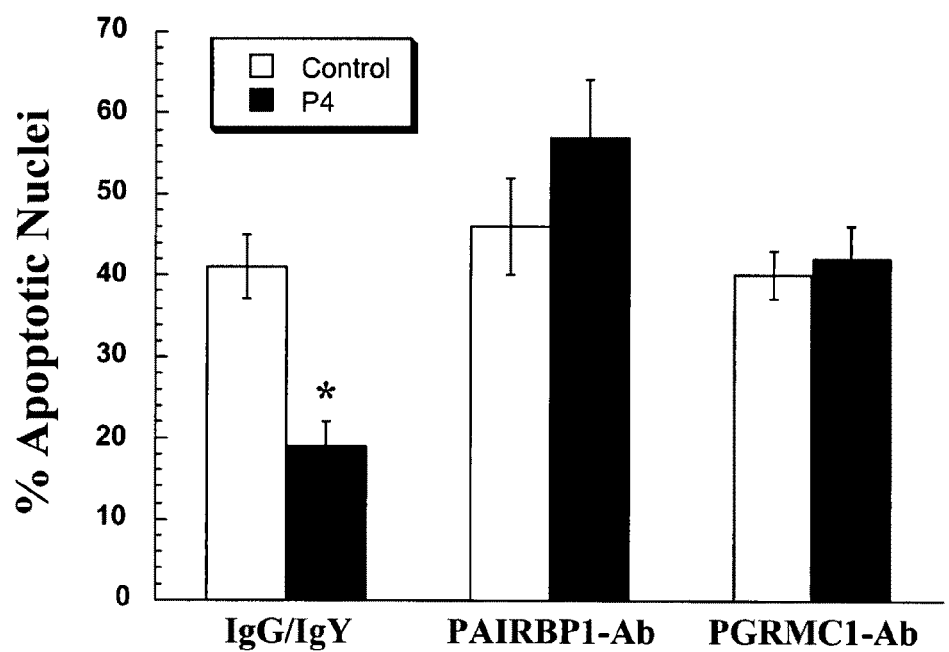
FIG. 3 is a bar graph of percent apoptotic nuclei showing the effect of PAIRBP1 and PGRMC1 antibodies on progesterone's anti-apoptotic action in human granulosa/luteal cells. In this experiment progesterone was used at 0.1 µM. Values in this graph are means ± SE of eight replicate cultures taken from 6 patients. The asterisk indicates a value that is different from the IgG/IgY control (p<0.05). The rate of apoptosis was assessed after one hour of culture.

In the presence of either IgG or IgY, 1 µM progesterone suppressed apoptosis due to serum-withdrawal. In contrast, antibodies to either PAIRBP1 or PGRMC1 completely attenuated progesterone's anti-apoptotic action in human granulosa/luteal cells (FIG. 3).

Example 2

Expression of PGRMC1 and PAIRBP1 in Human Ovarian Cancer Tissues

Figure 4:
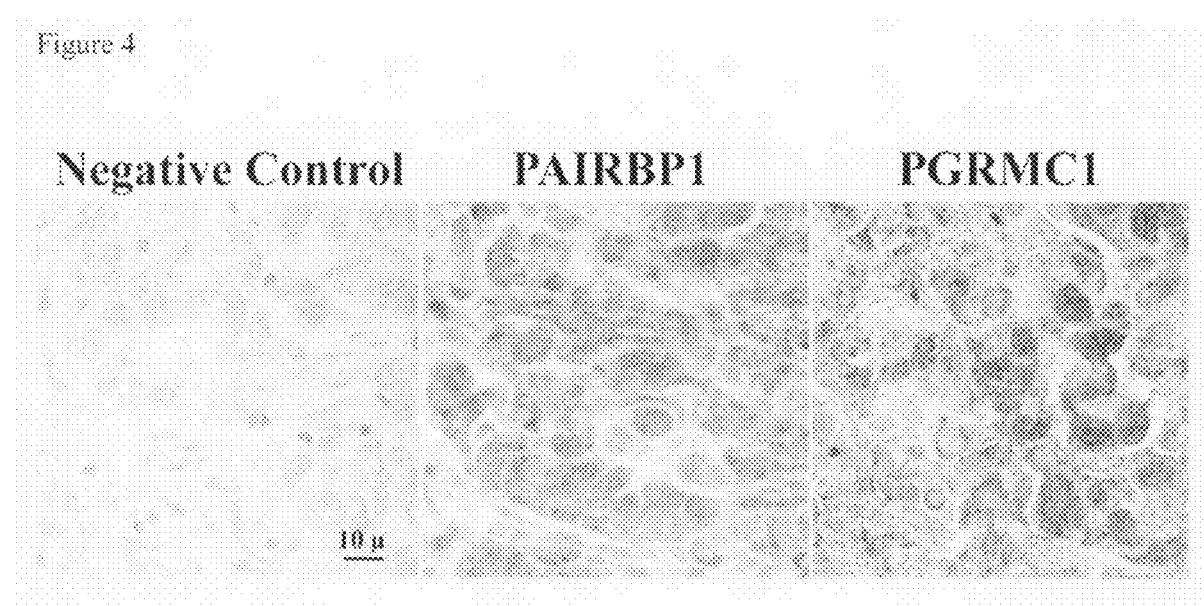
FIG. 4 is a reproduction of micrographs showing expression of PAIRBP1 (middle panel) and PGRMC1 (right panel) in ovarian cancer as assessed by immunohistochemistry. Each protein is revealed by the presence of a brown stain. A negative control is shown in the left panel.

Tissues were obtained from patients with Stage IV ovarian epithelial cell cancer and immunohistochemical studies were conducted as described above. Both PGRMC1 and PAIRBP1 are expressed in ovarian epithelial cancer cells (FIG. 4).

Example 3

Expression of PGRMC1 in Human Ovarian Cancer Tissues Not Expressing PGR

Tissues were obtained from patients with Stage III ovarian epithelial cell cancer and immunohistochemical studies were conducted as described above. PGRMC1 is highly expressed in ovarian tumors and even appears to increase in ovarian tumors that no longer express PGR (Compare FIGS. 5B and D with FIGS. 5A and C).

Example 4 siRNA Studies Using SIGC Cells

Figure 6A:
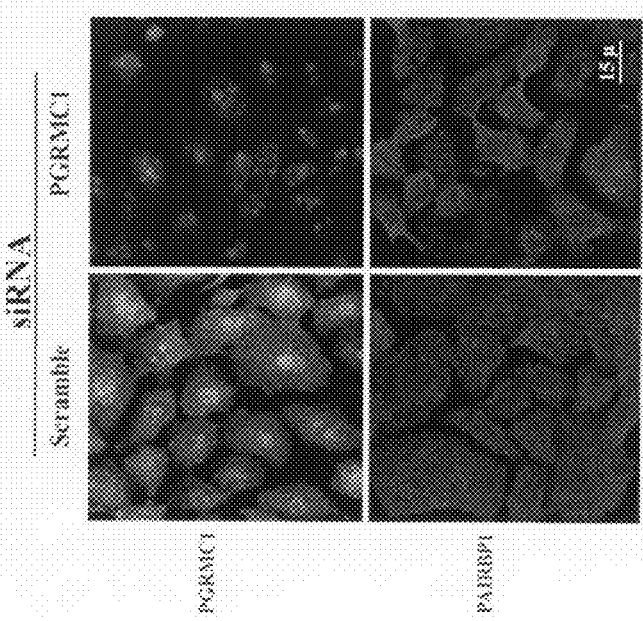
FIG. 6A is a scan of a micrograph showing the effect of PGRMC1 siRNA on the expression of PGRMC1.
Figure 6B:
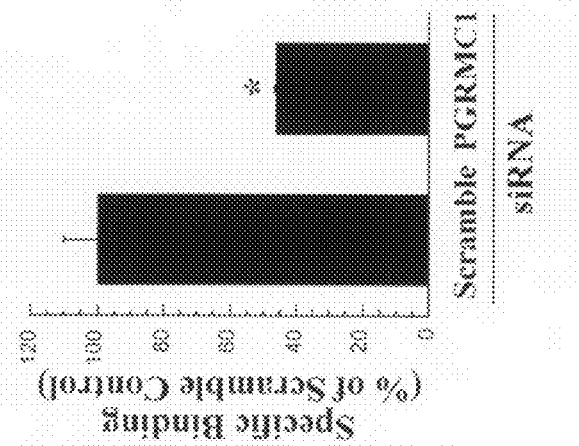
FIG. 6B is a bar graph showing the effect of PGRMC1 siRNA on specific $^3$H-PROGESTERONE binding.
Figure 6C:
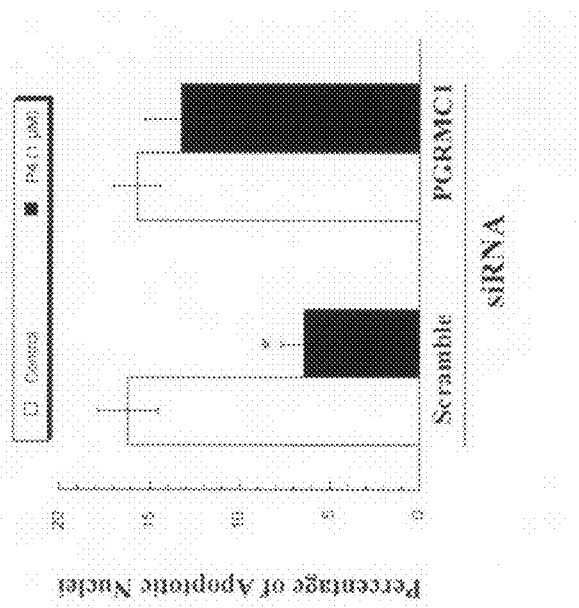
FIG. 6C is a bar graph showing the effect of PGRMC1 siRNA on progesterone's ability to inhibit apoptosis in SIGC cells. The asterisk indicates a value different from control.

Small interfering RNA (siRNA) studies were conducted with Spontaneously Immortalized Granulosa Cells (SIGC). These cells do not express the nuclear Progesterone Receptor (PGR) and therefore do not exhibit the nuclear (genomic) effects of progesterone. The SIGC cells do exhibit the non-genomic effects of progesterone thought to be mediated by the progesterone plasma membrane receptor complex. The cells and the methods for culturing them are described by Peluso et al., *Endocrinology* 147(6):3133-3140 (2006). The starting point for the conditions for delivery of siRNAs is the protocol provided by Ambion Inc. (Austin, Tex.), the source of the siRNAs used in these experiments. The experiments used the transfection conditions identified in GAPDH siRNA studies (i.e., 7 microliters of NeoFX transfection agent) that were sufficient to eliminate GAPDH levels. Within 24 hours of transfection with 30 nM predesigned PGRMC1 siRNA (Ambion siRNA ID 194475), PGRMC1 levels were virtually eliminated as assessed by immunocytochemistry. Scramble siRNA served as control (compare the amount of green fluorescence in cells treated with scramble siRNA verses PGRMC1 siRNA in FIG. 6A). Moreover, the depletion of PGRMC1 results in a significant decrease in the ability of these cells to specifically bind progesterone (FIG. 6B) and the complete attenuation of progesterone's ability to prevent apoptosis (FIG. 6C).

Example 5

PGRMC1 Mediates Progesterone's Anti-apoptotic Action Via its Interaction with PAIRBP1

In order to identify the amino acid sequence within PGRMC1 that interacts with PAIRBP1, a GFP-PGRMC1 deletion series was generated. The numbers associated with each mutant denote the amino acids they encode as shown (FIGS. 7B and 7C). The wild-type (1-194) PGRMC1 and its GFP-PGRMC1 mutants were tested for their effects on progesterone's anti-apoptotic action (FIG. 7B) and for the interaction site with PAIRBP1 (FIG. 7C).

While the wild-type (1-194) transduces progesterone's action, deleting any section results in an inability to mediate progesterone's action. Although there are different functional domains throughout PGRMC1 (structural organization of PGRMC1 in FIG. 7A), depletion of the first 20 amino acids leads to a rate of apoptosis that is even greater than the vector alone or the 1-130 mutant.

REFERENCES

All cited publications, patents, patent applications, sequence information cited by GenBank, Ensembl or other public sequence database accession numbers are specifically incorporated by reference herein in their entirety. In particular, the following references are hereby incorporated by reference herein in their entirety.

1. Peluso et al., "Progesterone Membrane Receptor Component 1 Expression in the Immature Rat Ovary and Its Role in Mediating Progesterone's Antiapoptotic Action", *Endocrinology* 147(6):3133-3140 (2006).
2. Peluso, "Multiplicity of Progesterone's Actions and Receptors in the Mammalian Ovary", *Biology of Reproduction* 75:2-8 (2006).
3. Peluso et al., "Expression and Function of PAIRBP1 Within Gonadotropin-Primed Immature Rate Ovaries: PAIRBP1 Regulation of Granulosa and Luteal Cell Viability", *Biology of Reproduction* 73:261-270 (2005).
4. Peluso et al., "Involvement of an Unnamed Protein, RDA288, in the Mechanism through which Progesterone Mediates Its Antiapoptotic Action in Spontaneously Immortalized Granulosa Cells", *Endocrinology* 145(6): 3014-3022 (2004).
5. Chaffkin et al., "The Role of Progesterone in Regulating Human Granulosa Cell Proliferation and Differentiation in Vitro." *J Clin Endocrinol Metab* 76(3):696-700 (1993).
6. Chaffkin et al., "Progesterone as an Autocrine/Paracrine Regulator of Human Granulosa Cell Proliferation", *J Clin Endocrinol Metab* 75(6):1404-1408 (1992).
7. Engmann et al., "Progesterone Regulation of Human Granulosa/Luteal Cell Viability by an RU486-Independent Mechanism" *J Clin Endocrinol Metab* 91(12): 4962-4968 (2006). 8. Losel et al., "Classic and Non-Classic Progesterone Receptors Are Both Expressed in Human Spermatozoa" *Horm. Metab. Res.* 37:10-4 (2005).

What is claimed is:

1. A pharmaceutical composition comprising a progesterone regulator in a pharmaceutically acceptable carrier, wherein the progesterone regulator is in an amount effective to inhibit a progesterone non-genomic action when administered to a mammal, wherein the progesterone regulator is a peptide that has about 20 to about 30 amino acids, and wherein the progesterone regulator comprises a peptide as shown in SEQ ID NO: 2.

2. The pharmaceutical composition of claim 1, wherein the progesterone regulator inhibits the progesterone non-genomic action by interacting with at least one of PGRMC1, PAIRBP1 and progesterone receptor complex.

3. The pharmaceutical composition of claim 1, wherein the progesterone regulator inhibits the progesterone non-genomic action by disrupting binding interaction between PGRMC1 and PAIRBP1.

4. The pharmaceutical composition of claim 1, wherein the progesterone regulator inhibits the progesterone non-genomic action by preventing progesterone from binding to progesterone receptor complex.

5. The pharmaceutical composition of claim 1, wherein the progesterone non-genomic action is an anti-apoptotic action and the progesterone regulator promotes apoptosis.

6. The pharmaceutical composition of claim 1 wherein the peptide has about 20 amino acids.

7. The pharmaceutical composition of claim 1, wherein the peptide consists of the amino acid sequence of SEQ ID NO:2.

8. The pharmaceutical composition of claim 1, further comprising a chemotherapeutic agent.

9. A method of treating endometriosis or ovarian cancer in a mammal comprising administering to the mammal a progesterone regulator, wherein the progesterone regulator inhibits a progesterone non-genomic action, wherein the progesterone regulator is a peptide that has about 20 to about 30 amino acids, and wherein the progesterone regulator comprises a peptide as shown in SEQ ID NO: 2.

* * * * *

SEQUENCE LISTING

```
<160> NUMBER OF SEQ ID NOS: 2

<210> SEQ ID NO 1
<211> LENGTH: 20
<212> TYPE: PRT
<213> ORGANISM: Homo sapiens

<400> SEQUENCE: 1

Met Ala Ala Glu Asp Val Val Ala Thr Gly Ala Asp Pro Ser Glu Leu
1               5                   10                  15

Glu Leu Leu Leu
            20

<210> SEQ ID NO 2
<211> LENGTH: 20
<212> TYPE: PRT
<213> ORGANISM: Homo sapiens

<400> SEQUENCE: 2

Met Ala Ala Glu Asp Val Val Ala Thr Gly Ala Asp Pro Ser Asp Leu
1               5                   10                  15

Glu Ser Gly Gly
            20
```